United States Patent

Ofner et al.

[11] Patent Number: 5,965,562
[45] Date of Patent: Oct. 12, 1999

[54] AROYL-PIPERIDINE DERIVATIVES

[75] Inventors: Silvio Ofner, Münchenstein; Siem Jacob Veenstra, Basel; Walter Schilling, Himmelried, all of Switzerland

[73] Assignee: Novartis Corporation, Summit, N.J.

[21] Appl. No.: 08/961,546

[22] Filed: Oct. 30, 1997

Related U.S. Application Data

[63] Continuation of application No. 08/541,358, Oct. 10, 1995, abandoned

[30] Foreign Application Priority Data

Oct. 14, 1994 [CH] Switzerland ............................ 3091942

[51] Int. Cl.$^6$ .................. A61K 31/445; A61K 31/47; A61K 31/505; C07D 401/12
[52] U.S. Cl. .................. 514/259; 514/307; 514/314; 514/319; 544/283; 546/146; 546/169; 546/205
[58] Field of Search .................. 546/146, 169, 546/205; 544/283; 514/307, 314, 319, 259

[56] References Cited

U.S. PATENT DOCUMENTS

| | | | |
|---|---|---|---|
| 5,102,667 | 4/1992 | Dubroeulq et al. | 424/489 |
| 5,126,455 | 6/1992 | Feldman et al. | 546/20 |
| 5,145,967 | 9/1992 | Lin et al. | 546/208 |
| 5,310,743 | 5/1994 | Schilling et al. | 514/311 |
| 5,317,020 | 5/1994 | Edmonds-Alt et al. | 514/255 |

FOREIGN PATENT DOCUMENTS

| | | |
|---|---|---|
| 9005525 | 5/1990 | WIPO . |
| 9118878 | 12/1991 | WIPO . |
| 9118899 | 12/1991 | WIPO . |
| 9206079 | 4/1992 | WIPO . |

OTHER PUBLICATIONS

Becker et al Chem Abstract 56: 7263i (1961).
Becker et al Chem Abstract 63:11494c (1965).
Becker et al Chem Abstract 68:38700v (1968).
Watling Tips vol. 13, pp. 266–269, Jul. 1992 "Nonpeptide Antagonists Herald New Era in Tachykinin Research."
McLean et al, Science 251, 437–439, Jan. 25, 1991 "Activity and Distribution of Binding Sites in Brain of a Nonpeptide Substance P(NK) Receptor Antagonist."
Snider et al Science 251, 435–437, Jan. 25, 1991 A potent nonpeptide substance 'P (NK) Receptor'.

*Primary Examiner*—Richard L. Raymond
*Attorney, Agent, or Firm*—Gregory D. Ferraro

[57] ABSTRACT

The invention relates to novel N-(3,5-bis-trifluoromethyl-benzoyl)-2-benzyl-4-(azanaphthoyl-amino)-piperidines of the formula

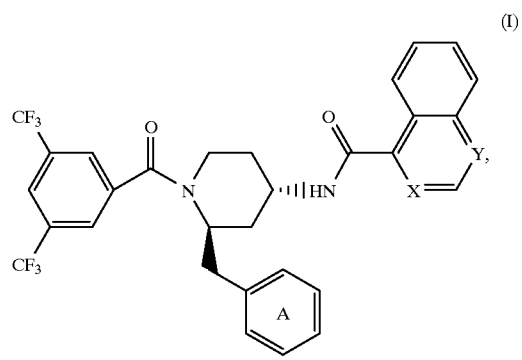

wherein X and Y are each independently of the other N and/or CH and the ring A is unsubstituted or mono- or poly-substituted by substituents selected from the group consisting of lower alkyl, lower alkoxy, halogen, nitro and trifluoromethyl; and the salts thereof, to the use thereof, to processes for the preparation thereof and to pharmaceutical compositions comprising a compound according to the invention or a pharmaceutically acceptable salt thereof.

14 Claims, No Drawings

AROYL-PIPERIDINE DERIVATIVES

This is a Continuation of Ser. No. 08/541,358, filed Oct. 10, 1995 now abandoned.

The invention relates to novel N-(3,5-bis-trifluoromethyl-benzoyl)-2-benzyl-4-(azanaphthoyl-amino)-piperidines of the formula

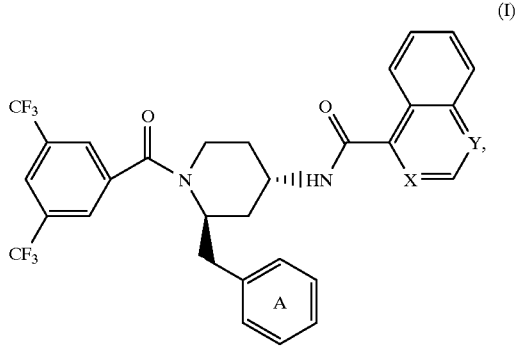

wherein X and Y are each independently of the other N and/or CH and the ring A is unsubstituted or mono- or poly-substituted by substituents selected from the group consisting of lower alkyl, lower alkoxy, halogen, nitro and trifluoromethyl; and the salts thereof, to the use thereof, to processes for the preparation thereof and to pharmaceutical compositions comprising a compound according to the invention or a pharmaceutically acceptable salt thereof.

The compounds of formula I may be present in the form of salts, especially pharmaceutically acceptable salts. Acid addition salts can be formed with the basic centre of the piperidine ring. Suitable as the acid component are, for example, strong inorganic acids, such as mineral acids, for example sulfuric acid, phosphoric acids, for example orthophosphoric acid, hydrohalic acids, for example hydrochloric acid, or strong organic carboxylic acids, such as unsubstituted or substituted, for example halo-substituted, lower alkanecarboxylic acids, for example acetic acid or trifluoroacetic acid, or saturated or unsaturated dicarboxylic acids, for example oxalic, malonic, succinic, maleic, fumaric, phthalic or terephthalic acid, or hydroxycarboxylic acids, for example ascorbic, glycolic, lactic, malic, tartaric or citric acid, amino acids, for example aspartic or glutamic acid, or benzoic acid, or organic sulfonic acids, such as unsubstituted or substituted, for example halo-substituted, lower alkanesulfonic acids, for example methanesulfonic acid, or unsubstituted or substituted, for example lower alkyl-substituted, arylsulfonic acids, for example p-toluenesulfonic acid. Salts that are not suitable for therapeutic use are also included; the latter salts can be used, for example, in the isolation or purification of free compounds of formula I or the pharmaceutically acceptable salts thereof. Only the pharmaceutically acceptable, non-toxic salts are used therapeutically and those are therefore preferred.

Since the compounds according to the invention have at least two optically active carbon atoms they may accordingly be present in the form of stereoisomers, stereoisomeric mixtures and in the form of the (substantially) pure diastereoisomers. The present invention relates also to corresponding stereoisomers.

Preference is given to compounds of formula I wherein the ring A is substituted.

Unless otherwise defined, the general terms used hereinbefore and hereinafter have the meanings given below.

The term "lower" denotes that groups and compounds so defined each have from 1 up to and including 7, preferably from 1 up to and including 4, carbon atoms.

Lower alkyl is, for example, methyl, ethyl, n-propyl, isopropyl, n-butyl, isobutyl, sec-butyl, tert-butyl or a corresponding pentyl, hexyl or heptyl radical. $C_1$–$C_4$alkyl is preferred.

Lower alkoxy is, for example, methoxy, ethoxy, n-propyloxy, isopropyloxy, n-butyloxy, iso-butyloxy, sec-butyloxy, tert-butyloxy or a corresponding pentyloxy, hexyloxy or heptyloxy radical. $C_1$–$C_4$alkoxy is preferred.

Halogen is especially halogen having an atomic number of up to and including 35, i.e. fluorine, chlorine or bromine, and also includes iodine. Chlorine is preferred.

Substance P is a naturally occurring undecapeptide of the tachykinin family. It is produced in mammals and acts pharmacologically as a neuropeptide. Substance P plays an important role in various disorders, for example in the case of painful conditions, in migraines and in certain disorders of the central nervous system, such as anxiety states, vomiting, schizophrenia and depression, and in certain motor disorders, such as Parkinson's disease, but also in inflammatory diseases, such as rheumatoid arthritis, iritis and conjunctivitis, in diseases of the respiratory organs, such as asthma and chronic bronchitis, in diseases of the gastrointestinal system, such as ulcerative colitis and Crohn's disease, and in hypertension.

A great deal of work is being done to advance the development of the field of substance-P-antagonists and, for example, to find suitable substance-P-antagonists having a broad spectrum of action that exhibit outstanding in vivo activity and increased bioavailability as well as improved chemical stability.

Extensive pharmacological studies have shown that the compounds according to the invention and the salts thereof antagonise substance P to an especially preferred extent and thus inhibit the symptoms induced by substance P.

The substance-P-antagonising effects can be demonstrated—as shown below—using test methods known to the person skilled in the art. Such effects are observed both in vitro and in vivo. For example, the substance-P-induced formation of phosphoinositol in human astrocytoma cells is antagonised in vitro by the compounds of formula I and IA and the pharmaceutically acceptable salts thereof. $IC_{50}$ values of from approximately 1 nmol are found. A suitable test model for the detection of that inhibition is, for example, the test method of Lee, C. M. et al., as described in J.Neurochem. 59, 406–414 (1992).

In addition, the binding of $^3$H-substance P to bovine retina in the radio receptor assay according to H. Bittiger, Ciba Foundation Symposium 91, 196–199 (1982) is inhibited with $IC_{50}$ values of from approximately 1 nmol. For example, the following in vitro values were obtained for the target compounds of Examples 3, 4 and 5: 7 nmol-6 nmol-6.9 nmol.

A change in behaviour is produced in gerbils by i.c.v. administration of substance P methyl ester. That effect can be inhibited in vivo after peroral administration of compounds of formulae I and IA and the salts thereof. The test method used is the method of A. Vassout et al., which was presented at the "Substance P and Related Peptides: Cellular and Molecular Physiology" Congress in Worchester, Mass., in 1990. In that method, $ED_{50}$ values of from approximately 0.1 mg/kg p.o. are obtained, demonstrating their usefulness in the treatment of disorders of the central nervous system.

In vivo, using the experimental procedure of Lundberg et al., Proc. Nat. Acad. Sci. (USA) 80, 1120–1124, the compounds of formulae I and IA and the salts thereof inhibit vagally induced bronchospasms in guinea pigs at a dose of from approximately 1.0 mg/kg i.v., which demonstrates their suitability for the treatment of asthma.

Compared with the corresponding compounds disclosed in the European Patent Application having the Publication No. 532 456 A1, the compounds according to the invention not only have markedly better in vivo activity, but they also exhibit substantially greater chemical stability, for example with respect to oxygen, and enhanced oral bioavailability.

The substance-P-antagonists of formulae I and IA prepared in accordance with the invention and the pharmaceutically acceptable salts thereof are accordingly outstandingly suitable for the therapeutic treatment of the pathological symptoms listed hereinbefore.

The invention relates also to a method of treating disorders induced by substance P by the administration of a therapeutically effective amount of a compound of formula I or IA or of a pharmaceutically acceptable salt thereof.

The present invention relates also to the use of a compound of formula I or IA or of a pharmaceutically acceptable salt thereof in the preparation of medicaments for the treatment of disorders induced by substance P.

The invention relates also to the use of compounds of formula I or IA or of the salts thereof as biochemical tools, for example for the identification and, possibly, the profiling of further potent substance-P-antagonists.

The invention relates especially to compounds of formula IA

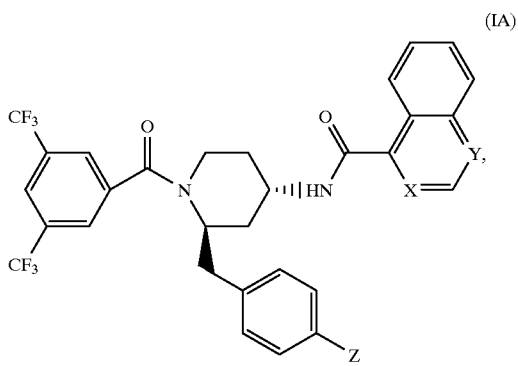

(IA)

wherein X is CH or N and Y is N, and Z is hydrogen, halogen or nitro, and to the salts thereof.

The invention relates above all to compounds of formula IA wherein X is N or CH and Y is N, and Z is halogen, such as chlorine, and to the salts thereof.

The invention relates specifically to the compounds of formula I mentioned in the Examples and to the salts thereof.

The invention relates also to processes for the preparation of the compounds according to the invention. Those processes comprise:

a) reacting a compound of formula (IIa)

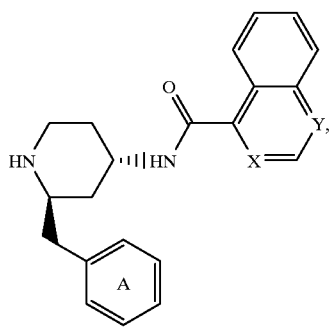

(IIa)

wherein X and Y are as defined and the ring A is unsubstituted or is substituted as indicated, with a compound of formula IIb

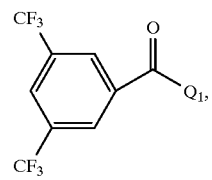

(IIb)

wherein $Q_1$ is free or etherified hydroxy, such as hydroxy, lower alkoxy or unsubstituted or substituted phenoxy, or is reactive esterified hydroxy, such as halogen, especially chlorine, or a radical of the formula

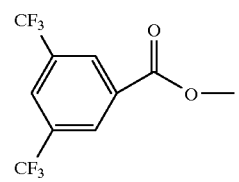

or with a salt thereof; or b) reacting a compound of formula (IIIa)

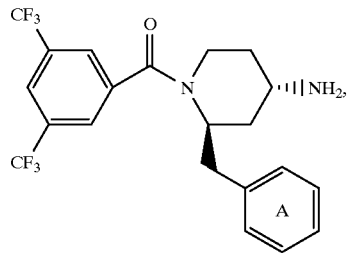

(IIIa)

wherein the ring A is unsubstituted or is substituted as indicated, with a compound of formula IIIb

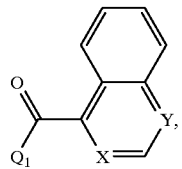

(IIIb)

wherein X and Y are as defined and $Q_1$ is free or etherified hydroxy, such as hydroxy, lower alkoxy or unsubstituted or substituted phenoxy, or is reactive esterified hydroxy, such as halogen, especially chlorine, or a radical of the formula

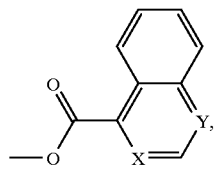

or with a salt thereof;
and, if desired, separating a mixture of isomers obtainable by the process and isolating the desired isomer and/or converting a free compound I or IA obtainable by the process into a salt or converting a salt of a compound I or IA obtainable by the process into the free compound I or IA or into a different salt.

Salts of starting materials having at least one basic centre, for example those of formula IIa or IIIa, are corresponding acid addition salts, while salts of starting materials having an acid group, for example those of formula IIb or IIIb, are in the form of salts with bases, in each case as described above in connection with corresponding salts of formulae I and IA.

The reactions described hereinbefore and hereinafter in the Variants are carried out in a manner known per se, for example in the absence or, generally, in the presence of a suitable solvent or diluent or a mixture thereof, the reactions being carried out as required with cooling, at room temperature or with heating, for example in a temperature range of from approximately −80° C. to the boiling temperature of the reaction medium, preferably from approximately −10° to approximately +200° C., and, if necessary, in a closed vessel, under pressure, in an inert gas atmosphere and/or under anhydrous conditions.

Process Variants a) and b)

The condensation to form the amide bond can be carried out in a manner known per se, for example as described in standard works, such as Houben-Weyl, "Methoden der organischen Chemie", 4th edition, Volume 15/II, Georg Thieme Verlag, Stuttgart 1974, "The Peptides" (E. Gross and J. Meienhofer, eds.), Volumes 1 and 2, Academic Press, London and New York, 1979/1980, or M. Bodanszky, "Principles of Peptide Synthesis", Springer-Verlag, Berlin 1984.

The condensation can be carried out in the presence of one of the customary condensation agents. Customary condensation agents are, for example, carbodiimides, for example diethyl-, dipropyl- or N-ethyl-N'-(3-dimethylaminopropyl)-carbodiimide or especially dicyclohexylcarbodiimide, also suitable carbonyl compounds, for example carbonyldiimidazole, 1,2-oxazolium compounds, for example 2-ethyl-5-phenyl-1,2-oxazolium-3'-sulfonate and 2-tert-butyl-5-methylisoxazolium perchlorate, or a suitable acylamino compound, for example 2-ethoxy-1-ethoxycarbonyl-1,2-dihydroquinoline, also activated phosphoric acid derivatives, for example diphenylphosphoryl azide, diethylphosphoryl cyanide, phenyl-N-phenylphosphoramidochloridate, bis(2-oxo-3-oxazolidinyl) phosphinic acid chloride or 1-benzotriazolyloxytris (dimethylamino)phosphonium hexafluorophosphate.

If desired, an organic base is added, for example a tri-lower alkylamine having bulky radicals, for example ethyl diisopropylamine, or a heterocyclic base, for example pyridine, 4-dimethylaminopyridine or preferably N-methylmorpholine.

The condensation of a carboxylic acid halide, for example with a corresponding amine, can be carried out also in the presence of a suitable base without the addition of a suitable coupling component.

The condensation is preferably carried out in an inert, polar, aprotic, preferably anhydrous, solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in a mixture thereof, as appropriate at reduced or elevated temperature, for example in a temperature range of from approximately −40° C. to approximately +100° C., preferably from approximately −10° C. to approximately +50° C., and if necessary under an inert gas atmosphere, for example a nitrogen atmosphere.

Reactive acid derivatives can also be formed in situ.

The starting material of formula (IIb) and (IIIb) is known or can be prepared in a manner known per se.

Compounds of formula (IIIa) can be prepared in a manner known per se. For example, a compound of the formula

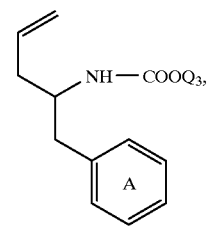

(IIIc)

wherein $Q_3$ is, for example, lower alkyl or phenyl-lower alkyl, as starting material, is N-alkylated, for example by reaction with lower alkoxy-halomethane, such as ethoxychloromethane, in the presence of a base, and the compound of formula (IIId)

(IIId)

thus obtainable, wherein $Q_4$ is, for example, lower alkyl, is treated with a nitrile, such as acetonitrile, in the presence of a strong acid, such as chlorosulfonic acid. In the resulting compound of formula (IIIe)

(IIIe)

the —C(═O)—OQ$_3$ group is removed by treatment with a strong acid, for example with hydrobromic acid.

For the preparation of an enantiomerically pure compound, in a compound of formula (IIIf)

(IIIf)

thus obtainable, the secondary amino group is acylated with an optically active compound, such as a corresponding O-acylated α-hydroxycarboxylic acid or a reactive derivative thereof, for example O-acetyl-(+)mandelic acid chloride, and the diastereoisomeric mixture thus obtainable is separated in a manner known per se, for example by chromatography. When the two N-acyl groups have been removed, for example by acid hydrolysis, for example with hydrochloric acid, a compound of formula (IIIg)

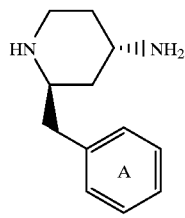

(IIIg)

is obtained.

The 4-amino group of compounds of formula (IIIg) is temporarily protected in a manner known per se, for example by reaction with benzaldehyde. Then the 3,5-bis-trifluoromethylbenzoyl group is introduced, for example as described for Process variant a), by coupling with a compound of formula (IIb), and the protecting group of the 4-amino group is removed, for example by treatment with an acid, such as hydrochloric acid, and a corresponding compound of formula (IIIa) is thus obtained.

Compounds of formula (IIa) can be prepared in a manner known per se. For example, a compound of formula (IIIg) is used as starting material and is coupled, for example as described for Process variant b), with a compound of formula (IIIb) in the presence of a coupling reagent, and the corresponding (aza-)naphthoyl group is thus introduced. A corresponding compound of formula (IIa) is thus obtained.

The invention is illustrated especially by the Examples and relates also to the novel compounds mentioned in the Examples and to the processes for the preparation thereof.

Resulting salts can be converted in a manner known per se into the free compounds, for example by treatment with a base, such as an alkali metal hydroxide, a metal carbonate or metal hydrogen carbonate, or ammonia, or another of the salt-forming bases mentioned at the beginning, or with an acid, such as a mineral acid, for example with hydrochloric acid, or another of the salt-forming acids mentioned at the beginning.

Resulting salts can be converted into different salts in a manner known per se: acid addition salts, for example, by treatment with a suitable metal salt, such as a sodium, barium or silver salt, of a different acid in a suitable solvent in which an inorganic salt being formed is insoluble and is therefore eliminated from the reaction equilibrium, and basic salts by freeing of the free acid and conversion into a salt again.

The compounds of formula I and IA, including their salts, may also be obtained in the form of hydrates or may include the solvent used for crystallisation.

As a result of the close relationship between the novel compounds in free form and in the form of their salts, hereinabove and hereinbelow any reference to the free compounds and their salts is to be understood as including also the corresponding salts and free compounds, respectively, as appropriate and expedient.

Resulting mixtures of diastereoisomers and mixtures of racemates can be separated in known manner into the pure diastereoisomers or racemates on the basis of the physico-chemical differences between the constituents, for example by chromatography and/or fractional crystallisation.

Resulting racemates can also be separated into the optical antipodes by known methods, for example by recrystallisation from an optically active solvent, with the aid of microorganisms or by reaction of the resulting diastereoisomeric mixture or racemate with an optically active auxiliary compound, for example according to the acidic, basic or functionally modifiable groups present in compounds of formulae I and IA with an optically active acid, base or an optically active alcohol, into mixtures of diastereoisomeric salts or functional derivatives, such as esters, and separation thereof into the diastereoisomers from which the desired enantiomer can be freed in the appropriate customary manner. Examples of suitable bases, acids and alcohols are optically active alkaloid bases, such as strychnine, cinchonine or brucine, or D- or L-(1-phenyl)ethylamine, 3-pipecoline, ephedrine, amphetamine and similar synthetically obtainable bases, optically active carboxylic or sulfonic acids, such as quinic acid or D- or L-tartaric acid, D- or L-di-o-toluyltartaric acid, D-or L-malic acid, D- or L-mandelic acid, or D- or L-camphorsulfonic acid, or optically active alcohols, such as borneol or D- or L-(1-phenyl)ethanol.

The invention relates also to those forms of the process in which a compound obtainable as intermediate at any stage of the process is used as starting material and the remaining steps are carried out, or in which a starting material is used in the form of a salt or, especially, is formed under the reaction conditions.

The invention relates also to the novel starting materials developed specifically for the preparation of the compounds of the invention, especially to those starting materials resulting in the compounds of formulae I and IA that were described at the beginning as being preferred, to processes for the preparation thereof and to their use as intermediates, including the compound (2R*,4S*)-N-[1-(3,5-bis-trifluoromethyl-benzoyl)-2-(4-nitro-benzyl)-piperidin-4-yl]-acetamide.

The novel compounds of formulae I and IA can be used, for example, in the form of pharmaceutical compositions that comprise a therapeutically effective amount of the active ingredient, optionally together with inorganic or organic, solid or liquid, pharmaceutically acceptable carriers that are suitable for enteral, for example oral, or parenteral administration. There are used, for example, tablets or gelatin capsules that comprise the active ingredient together with diluents, for example lactose, dextrose, saccharose, mannitol, sorbitol, cellulose and/or lubricants, for example silica, talc, stearic acid or salts thereof, such as magnesium or calcium stearate, and/or polyethylene glycol. Tablets can also comprise binders, for example magnesium aluminium silicate, starches, such as corn, wheat, rice or arrowroot starch, gelatin, tragacanth, methylcellulose, sodium carboxymethylcellulose and/or polyvinylpyrrolidone, and, if desired, disintegrators, for example starches, agar, alginic acid or a salt thereof, for example sodium alginate, and/or effervescent mixtures, or absorbents, colourings, flavourings and sweeteners. The novel compounds of formulae I and IA can also be used in the form of parenterally administrable compositions or in the form of infusion solutions. Such solutions are preferably isotonic aqueous solutions or suspensions which, for example in the case of lyophilised compositions that comprise the active ingredient on its own or together with a carrier, for example mannitol, can be prepared before use. The pharmaceutical compositions may be sterilised and/or may comprise excipients, for example preservatives, stabilisers, wetting agents and/or emulsifiers, solubilisers, salts for regulating the osmotic pressure and/or buffers. The pharmaceutical compositions in question, which, if desired, may comprise further pharmacologically active substances, are prepared in a manner known per se, for example by means of conventional mixing, granulating, confectioning, dissolving or lyophilising processes, and comprise from approximately 0.1% to 100%, especially from approximately 1% to approximately 50%, in the case of lyophilisates up to approximately 100%, active ingredient.

The invention relates also to the use of the compounds of formulae I and IA, preferably in the form of pharmaceutical compositions. The dose can depend on various factors, such as the mode of administration, species, age and/or individual condition. The daily doses to be administered are, in the case of oral administration, from approximately 0.25 to approximately 10 mg/kg, and in the case of warm-blooded animals having a body weight of approximately 70 kg, they are preferably from approximately 20 mg to approximately 500 mg.

The following Examples illustrate the invention; temperatures are given in degrees Celsius and pressures in mbar.

EXAMPLE 1
(2R,4S)-N-[1-(3,5-Bis-trifluoromethyl-benzoyl)-2-benzyl-piperidin-4-yl]-quinoline-4-carboxamide 2.95 g (11.6 mmol) of bis(2-oxo-3-oxazolidinyl) phosphinic acid chloride are added at 0° C. to a solution of 4.16 g (9.67 mmol) of (2R,4S)-2-benzyl-1-(3,5-bis-trifluoromethyl-benzoyl)-4-piperidineamine [EP 532 456 A1, Example 38 f], 1.84 g (10.6 mmol) of quinoline4-carboxylic acid and 3 ml (21.3 mmol) of triethylamine in 30 ml of methylene chloride and the ice bath is removed after 10 minutes. The reaction mixture is stirred for 4 hours at room temperature and then diluted with methylene chloride. The organic phase is extracted with aqueous 10% citric acid and with 1 N potassium carbonate solution, washed with brine, dried over magnesium sulfate and concentrated to dryness by evaporation. The crude product is chromatographed on silica gel with methylene chloride/acetone (7:3). The title compound is crystallised from methylene chloride/ether/hexane in the form of white crystals. M.p.: 187° C.; TLC: methylene chloride/acetone (7:3) $R_f$=0.48, FD-MS: $M^+$=585; [alpha]D=+9.9 (c=1, methylene chloride); analysis: calc.: C=63.59%, H=4.30%, N=7.18%, F=19.47%, found: C=63.50%, H=4.40%, N=7.16%, F=19.45%.

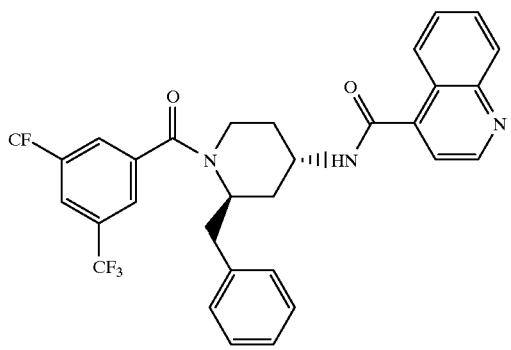

EXAMPLE 2
(2R,4S)-N-[1-(3,5-Bis-trifluoromethyl-benzoyl)-2-benzyl-piperidin-4-yl]-quinazoline-4-carboxamide Analogously to Example 1, 252 mg (1.45 mmol) of (2R,4S)-2-benzyl-1-(3,5-bis-trifluoromethyl-benzoyl)-4-piperidineamine in 5 ml of methylene chloride are reacted with 368 mg (1.45 mmol) of bis(2-oxo-3-oxazolidinyl) phosphinic acid chloride, 440 mg (4.35 mmol) of triethylamine and 566 mg (1.32 mmol) of quinazoline-4-carboxylic acid. The title compound is obtained in the form of white crystals. M.p.: 92–172° C.; TLC: hexane/ethyl acetate (1:1) $R_f$=0.37, FD-MS: $M^+$=586; [alpha]D=+1.3 (c=0.98, methylene chloride).

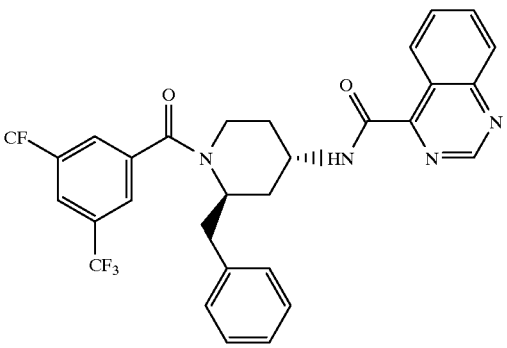

EXAMPLE 3
(2R,4S)-N-[1-(3,5-Bis-trifluoromethyl-benzoyl)-2-(4-chloro-benzyl)-piperidin-4-yl]-quinoline4-carboxamide A solution of 1.70 g (3.65 mmol) of (2R,4S)-1-(3,5-bis-trifluoromethyl-benzoyl)-2-(4-chloro-benzyl)-piperidine4-amine and 1.5 ml (10.96 mmol) of triethylamine in 3 ml of methylene chloride is added dropwise at 0° C. to a solution of 0.915 g (4.01 mmol) of quinoline4-carboxylic acid chloride hydrochloride [Nicolaï E, Güngör T, Goyard J, Cure G, Fouquet A, Teulon J M, Delchambre C, Cloarec A, Eur. J. Med. Chem., 1992, 27, 977] in 10 ml of methylene chloride. After 15 hours, a further 228 mg (1.0 mmol) of quinoline-4-carboxylic acid chloride hydrochloride and a further 0.1 ml (1.0 mmol) of triethylamine are added and the mixture is stirred for 3 hours. 1 N hydrochloric acid is added to the mixture which is then extracted with ethyl acetate. The organic phase is washed with 1 N sodium hydroxide solution and with brine, dried over sodium sulfate and concentrated. The residue is crystallised from toluene and yields the title compound in the form of white crystals. M.p. 204–207° C. (phase transition 135–140° C.); TLC: ethyl acetate: $R_f$=0.48, FD-MS: $M^+$=619(621).

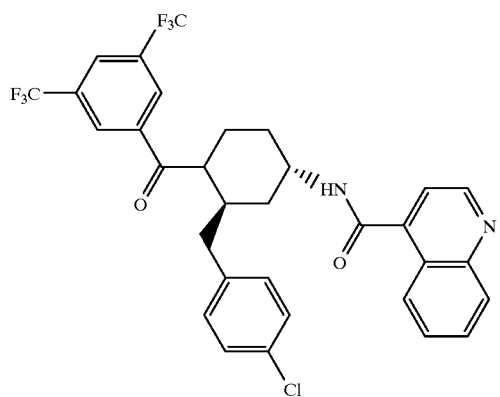

The starting material can be prepared, for example, as follows:

a) N-[1-(4-Chloro-benzyl)-but-3-enyl]-N-ethoxymethyl-carbamic acid methyl ester

A suspension of 10.0 g of sodium hydride (80% in mineral oil, 333 mmol) in dry tetrahydrofuran [THF] is heated at reflux under argon. A solution of 60.5 g (238 mmol) of [1-(4-chloro-benzyl)-but-3-enyl]-carbamic acid methyl ester [McCarty F J, Rosenstock P D, Paolini J P, Micucci D D, Ashton L, Bennetts W W, J. Med. Chem, 1968, 11(3),534] in 50 ml of dry THF is added dropwise thereto in the course of 1 hour. The mixture is then boiled under reflux for 2 hours until the evolution of gas subsides. The mixture is cooled to 0° C. and chloromethyl ethyl ether is added dropwise in such a manner that the reaction temperature does not exceed 5° C. The mixture is then heated slowly to 25° C. and stirred for 12 hours to complete the reaction. Excess sodium hydride is destroyed carefully with 1 ml of water before more water is added. The phases are separated and the aqueous phase is extracted again with tert-butyl methyl ether. The combined organic phases are washed with brine, dried over sodium sulfate, and concentrated by evaporation. The crude product is distilled at 0.1 mbar and has a boiling range of 120–125° C. TLC: ethyl acetate/hexane (1:6) $R_f$=0.34, FD-MS: $M^+$=311 (313).

b) (2R*,4S*)-4-Acetylamino-2-(4-chloro-benzyl)-piperidine-1-carboxylic acid methyl ester At −40° C., 20.6 ml (308 mmol) of chlorosulfonic acid are introduced into 500 ml of acetonitrile. A solution of 48.0 g (154 mmol) of N-[1-(4-chloro-benzyl)-but-3-enyl]-N-ethoxymethyl-carbamic acid methyl ester in 50 ml of acetonitrile is added dropwise in such a manner that the reaction temperature does not exceed −10° C. The mixture is then stirred for 20 minutes at −15° C. before 370 ml of 2 N sodium hydroxide solution and 100 ml of 10% aqueous sodium hydrogen carbonate solution are added to the reaction. The phases are separated and the aqueous phase is then extracted twice with toluene. The combined organic phases are dried over sodium sulfate. The crude product is crystallised from toluene and yields the title compound in the form of white crystals. M.p.: 169–170° C. TLC: methylene chloride/methanol/conc. ammonia (90:9:1) $R_f$=0.42, FD-MS: $M^+$=325.

c) (2R*,4S*)-N-[2-(4-Chloro-benzyl)-piperidin-4-yl]-acetamide 51.8 ml of 33% hydrogen bromide in acetic acid are added to (2R*,4S*)-4-acetylamino-2-(4-chloro-benzyl)-piperidine-1-carboxylic acid methyl ester (30.0 g, 92.3 mmol). After 16 hours, 200 ml of water are added to the mixture which is then washed twice with toluene. The aqueous phase is rendered basic and extracted twice with ethyl acetate. The organic phases are dried on potassium carbonate and concentrated by evaporation using a rotary evaporator. The title compound crystallises in the form of a hydrochloride from EtOH/ethyl acetate. M.p.: 288–289° C. TLC: methylene chloride/methanol/conc. ammonia (90:9:1) $R_f$=0.17, FD-MS: $(M+1)^+$=267.

d) (2'S,2R,4S)-Acetic acid 2-[4-acetylamino-2-(4-chloro-benzyl)-piperidin-1-yl]-2-oxo-1-phenyl-ethyl ester Racemic N-[2-(4-chloro-benzyl)-piperidin-4-yl]-acetamide hydrochloride (20.5 g, 67.6 mmol) is introduced with vigorous stirring at 0° C. into 34 ml of 2 N sodium hydroxide solution, 150 ml of a 10% aqueous sodium hydrogen carbonate solution and 50 ml of methylene chloride. In the course of 1 hour, S(+)-O-acetyl-mandelic acid chloride [Pracejus G,*Ann.*, 1959, 622, 10] (14.9 g, 70 mmol) is added dropwise thereto. The mixture is then stirred for 1 hour at +4° C. The phases are separated, and the organic phase is dried over sodium sulfate and concentrated by evaporation using a rotary evaporator. The title compound is isolated in the form of the pure diastereoisomer after crystallisation twice from methylene chloride/tert-butyl methyl ether. M.p.: 209–211° C. TLC: methylene chloride/isopropanol (9:1) $R_f$=0.65, FD-MS: $M^+$=443. [alpha]D=+77.50 (c=1, methylene chloride).

The mother liquors comprise mainly the non-crystalline diastereoisomer (2'S,2S,4R)-N-[2-(4-chloro-benzyl)-1-(acetoxy-phenyl-acetyl)piperidin-4-yl]-acetamide. TLC: methylene chloride/isopropanol (9:1) $R_f$=0.70.

e) (2R,4S)-1-(3,5-Bis-trifluoromethyl-benzoyl)-2-(4-chloro-benzyl)-piperidine-4-amine (2'S,2R,4S)-Acetic acid 2-[4-acetylamino-2-(4-chloro-benzyl)-piperidin-1-yl]-2-oxo-1-phenyl-ethyl ester (37.4 g, 84.5 mmol) is boiled under reflux for 2 days in 370 ml of 6 N hydrochloric acid. After cooling, the mixture is rendered basic with solid sodium hydroxide and extracted with methylene chloride. The combined organic phases are dried over potassium carbonate and concentrated by evaporation using a rotary evaporator. 8.5 ml (84.5 mmol) of benzaldehyde are added to the residue, which consists of almost pure (2R, 4S)-2-(4-chloro-benzyl)-piperidine-4-amine (19.0 g, 84.5 mmol, 100%), and the mixture is concentrated twice using a rotary evaporator with 150 ml of toluene. The oily residue is taken up in 180 ml of methylene chloride and 15.3 ml (110 mmol) of triethylamine and cooled to 10° C. Bis-trifluoromethylbenzoyl chloride (25.7 g, 92.9 mmol) is added dropwise over a period of 15 minutes and the mixture is then stirred for 1 hour at 25° C. to complete the reaction. 250 ml of 1 N-hydrochloric acid are added to the reaction mixture and the methylene chloride is removed under reduced pressure using a rotary evaporator. Hexane and ethanol are added until two homogeneous phases form. The organic phase is separated off and washing with hexane is continued until all the benzaldehyde has been removed. The mixture is rendered basic with solid sodium hydroxide and extracted repeatedly with methylene chloride. The organic phases are dried over sodium sulfate and concentrated using a rotary evaporator. Crystallisation from tert-butyl methyl ether/hexane yields the title compound in the form of white crystals. M.p.: 79–81° C. TLC: methylene chloride/methanol/conc. ammonia (90:9:1) $R_f$=0.21, FD-MS: $(M+1)^+$=465. [alpha]D=−12.7° (c=1, methylene chloride).

EXAMPLE 4

(2R,4S)-N-[1-(3,5-Bis-trifluoromethyl-benzoyl)-2-(4-chloro-benzyl)-piperidinyl]-quinazoline-4-carboxamide The ammonium salt of quinazoline-4-carboxylic acid (0.238 g, 1.25 mmol, [5]) is dissolved in methanol and 1 ml of triethylamine is added thereto. The solution is concentrated using a rotary evaporator. That procedure is repeated twice and yields the triethylammonium salt of quinazoline-4-carboxylic acid in the form of an oil which, together with 0.465 g (1.0 mmol) of (2R,4S)-1-(3,5-bis-trifluoromethyl-benzoyl)-2-(4-chloro-benzyl)-piperidine-4-amine and 0.175 ml of triethylamine, is dissolved in 10 ml of methylene chloride. Then at 0° C., 0.316 g (1.25 mmol) of bis(2-oxo-3-oxazolidinyl)phosphinic acid chloride is added and the ice bath is removed after 10 minutes. The reaction mixture is stirred for 4 hours at room temperature and then diluted with ethyl acetate. The organic phase is washed with aqueous 10% sodium hydrogen carbonate solution and brine, dried over sodium sulfate and concentrated to dryness by evaporation. The crude product is chromatographed with ethyl actate/hexane (1:2). The title compound is crystallised from ethyl acetate/hexane in the form of white crystals. M.p.: 118–120° C.; TLC: ethyl acetate/hexane (1:1) $R_f$=0.42; FD-MS: $M^+$=620; [alpha]D=−15.7 (c=1, methylene chloride); analysis: calc.: C=58.03%, H=3.73%, N=9.05%, found: C=57.9%, H=3.7%, N=8.9%.

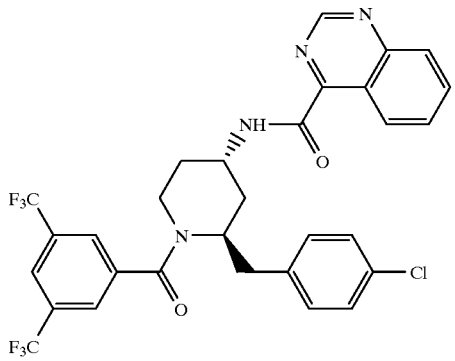

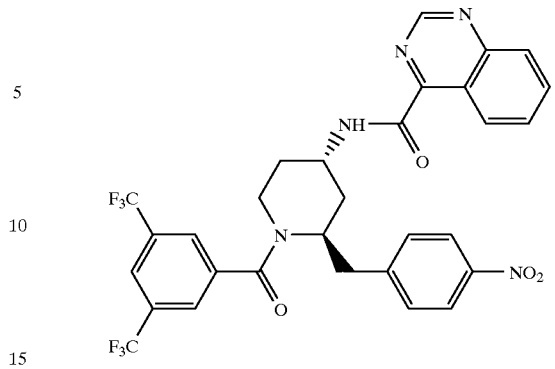

EXAMPLE 5

(2R,4S)-N-[1-(3,5-Bis-trifluoromethyl-benzoyl)-2-(4-chloro-benzyl)-piperidinyl]-isoquinoline-1-carboxamide Analogously to Example 1, 0.30 g (0.64 mmol) of (2R, 4S)-1-(3,5-bis-trifluoromethyl-benzoyl)-2-(4-chloro-benzyl)-piperidine-4-amine in 8 ml of methylene chloride is reacted with 0.18 g (0.71 mmol) of bis(2-oxo-3-oxazolidinyl)phosphinic acid chloride, 0.18 ml (1.30 mmol) of triethylamine and 0.112 g (0.64 mmol) of isoquinoline-1-carboxylic acid. The crude product is chromatographed with ethyl acetate/hexane (1:3). The title compound is crystallised from ethyl acetate/hexane in the form of white crystals. M.p.: 112–113° C.; TLC: ethyl acetate/hexane (1:2) $R_f$=0.30; FD-MS: $M^+$=619(621); [alpha]D=−11.3 (c=1, EtOH); analysis: calc.: C=60.06%, H=3.90%, N=6.78%, found: C=61.0%, H=4.5%, N=6.4%.

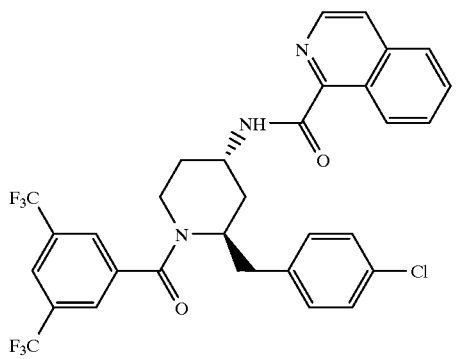

EXAMPLE 6

(2R,4S)-N-[1-(3,5-Bis-trifluoromethyl-benzoyl)-2-(4-nitro-benzyl)-piperidinyl]-quinazoline-4-carboxamide Analogously to Example 4, 0.14 g (0.29 mmol) of (2R*, 4S*)-1-(3,5-bis-trifluoromethyl-benzoyl)-2-(4-nitro-benzyl)-piperidine4-amine in 5 ml of methylene chloride is reacted with 0.083 g (0.32 mmol) of bis(2-oxo-3-oxazolidinyl)phosphinic acid chloride, 0.11 ml (0.75 mmol) of triethylamine and 0.058 g (0.30 mmol) of the ammonium salt of quinazoline-4-carboxylic acid [Armarego W L F and Smith J I C, *J. Chem. Soc.* (B), 1967, 449]. The crude product is chromatographed with ethyl acetate/hexane (1:3). The title compound crystallises from ethyl acetate/hexane in the form of white crystals. M.p.: 112–113° C.; TLC: methylene chloride/methanol (19:1) $R_f$=0.55; FD-MS: $M^+$=631.

The starting material can be prepared, for example, as follows:

a) [1-(4-Nitro-benzyl)-but-3-enyl]-carbamic acid benzyl ester

In the presence of triethylamine (5.6 ml, 40.0 mmol) and benzyl alcohol (5.18 g, 48.0 mmol) in toluene, 11.55 g (42.0 mmol) of phosphoric acid diphenyl ester azide are added at 50° C. to 2-(4-nitro-benzyl)-pent-4-enecarboxylic acid [2-(4-nitro-benzyl)-pent-4-enoic acid is prepared analogously to 2-(4-chloro-benzyl)-pent-4-enoic acid, see *J. Med. Chem*, 1968, 11(3), 5341 (9.3 g, 40.0 mmol). After 20 minutes the temperature is increased slowly and the mixture is then maintained under reflux for 3 hours. After cooling, the reaction mixture is washed twice with 1 N sodium hydroxide solution, twice with 1 N hydrochloric acid and twice with brine, dried over sodium sulfate and concentrated by evaporation using a rotary evaporator. After crystallisation of the crude product from toluene/hexane, the title compound is obtained in the form of white crystals. M.p.: 94–95° C. TLC: ethyl acetate/hexane (1:3) $R_f$=0.22.

b) N-[1-(4-Nitro-benzyl)-but-3-enyl]-N-ethoxymethyl-carbamic acid benzyl ester

A mixture of 10 ml of aqueous 50% sodium hydroxide solution, 25 ml of methylene chloride and 130 mg (0.4 mmol) of benzyltributylammonium chloride is stirred vigorously at 5–10° C. After the addition of 1-(4-nitro-benzyl)-but-3-enyl]-carbamic acid benzyl ester (6.8 g, 20.0 mmol), 2.64 g (28 mmol) of chloromethylethyl ether are added dropwise over a period of 2 hours. The mixture is then stirred for 1 hour at room temperature, diluted with ice and water and extracted with methylene chloride. The organic phase is dried over sodium sulfate, concentrated to dryness by evaporation and chromatographed on silica gel with hexane/ethyl acetate (10:1). The title compound is obtained in the form of a colourless oil. TLC: ethyl acetate/hexane (1:3) $R_f$=0.41. FD-MS: $M^+$:398.

c) (2R*,4S*)-4-Acetylamino-2-(4-nitro-benzyl)-piperidine-1-carboxylic acid benzyl ester Analogously to Example 3b, 5.0 g (12.6 mmol) of N-[1-(4-nitro-benzyl)-but-3-enyl]-N-ethoxy-methyl-carbamic acid benzyl ester are reacted with 1.77 g (25.2 mmol) of chlorosulfonic acid in acetonitrile. Chromatography on silica gel (methylene chloride/methanol (95:5)) yields the title compound in the form of a colourless resin. TLC: methylene chloride/methanol (9:1) $R_f$=0.40. FD-MS: $(M+H)^+$:412.

d) (2R*,4S*)-N-[2-(4-Nitro-benzyl)-piperidin-4-yl]-acetamide

Concentrated hydrochloric acid is added to (2R*,4S*)-4-acetylamino-2-(4-nitro-benzyl)-piperidine-1-carboxylic acid benzyl ester (2.65 g, 6.45 mmol) and the mixture is heated at 55° C. for 2 hours, the evolution of gas occurring. The reaction mixture is washed twice with hexane and concentrated by evaporation under reduced pressure using a rotary evaporator. The title compound is obtained as a hydrochloride in the form of white crystals containing 3 molecules of water of crystallisation. M.p.: >250° C. TLC: methylene chloride/methanol/conc. ammonia (90:9:1) $R_f$=0.29. $^1$H-NMR (200 MHz, $D_2O$): δ 8.26 (d, 2H), 7.59 (d, 2H), 4.26–4.17 (m,1H), 3.90–3.72 (m, 1H), 3.40–3.02(m, 4H), 1.99 (s, 3H), 2.06–1.75 (m, 4H).

e) (2R*,4S*)-N-[1-(3,5-Bis-trifluoromethyl-benzoyl)-2-(4-nitro-benzyl)-piperidin-4-yl]-acetamide 2.49 g (9.0 mmol) of 3,5-bis-trifluoromethylbenzoyl chloride are added in the course of 1 hour at 0–5° C. to a stirred suspension of 2.50 g (9.0 mmol) of (2R*,4S*)-N-[2-(4-nitro-benzyl)-piperidin-4-yl]-acetamide in 20 ml of methylene chloride and 20 ml of a 10% aqueous sodium hydrogen carbonate solution. The mixture is then stirred for 1 hour at 25° C. The organic phase is dried over sodium sulfate, concentrated to dryness by evaporation and chromatographed on silica gel with methylene chloride/methanol. The title compound is obtained in the form of a yellowish resin. TLC: methylene chloride/methanol/conc. ammonia (90:9:0.5) $R_f$=0.45. $^1$H-NMR (200 MHz, $D_2O$): rotameric mixture. δ 8.28–7.08 (m, 7H), 5.41 (br d, NH), 5.36–5.20 (m, 0.5H), 4.87–4.73 (m, 0.5H), 4.51–4.30 (m, 1H), 4.00–3.82 (m, 0.5H), 3.60–2.85 (m, 3.5H), 1.98 (s, 3H), 2.30–1.92 (m, 2H), 1.62–1.22 (m, 2H).

f) (2R*,4S*)-N-Acetyl-N-[1-(3,5-bis-trifluoromethyl-benzoyl)-2-(4-nitro-benzyl)-piperidin-4-yl]-carbamic acid tert-butyl ester 5.32 g (24.0 mmol) of di-tert-butyl dicarbonate are added in portions to a solution, stirred at 50° C., of 6.9 g (13.34 mmol) of (2R*,4S*)-N-[1-(3,5-bis-trifluoromethyl-benzoyl)-2-(4-nitro-benzyl)-piperidin-4-yl]-acetamide, 1.62 g (13.34 mmol) of 4-N,N-dimethylaminopyridine and 2.02 g (20.0 mmol) of triethylamine in 25 ml of toluene. The reaction mixture is then stirred for 18 hours at 50° C. After cooling, the reaction mixture is diluted with ethyl acetate, washed with dilute hydrochloric acid to pH 3 and then with brine. The organic phase is dried over sodium sulfate, concentrated to dryness by evaporation and chromatographed on silica gel (hexane/ethyl acetate 2:1). The title compound is obtained in the form of a yellow solid. TLC: ethyl acetate/hexane (1:2) $R_f$=0.40. FD-MS: M$^+$:617.

g) (2R*,4S*)-1-(3,5-Bis-trifluoromethyl-benzoyl)-2-(4-nitro-benzyl)-piperidine-4-amine A solution of 200 mg (0.32 mmol) of (2R*,4S*)-N-acetyl-N-[1-(3,5-bis-trifluoromethyl-benzoyl)-2-(4-nitro-benzyl)-piperidin-4-yl]-carbamic acid tert-butyl ester is added in 5 ml of methanol to a solution, stirred under an inert gas, of 0.04 ml (0.06 mmol) of n-butyllithium in hexane (1.6 M). After 1 hour, 5 mg (0.08 mmol) of acetic acid are added and the mixture is concentrated to dryness by evaporation. The residue is taken up in 2 ml of methylene chloride and 1.2 ml of trifluoroacetic acid and the mixture is stirred for 2.5 hours at room temperature. The mixture is diluted with methylene chloride and washed with 2 N sodium hydroxide solution. The organic phase is dried over sodium sulfate, filtered and concentrated to dryness. The title compound is obtained in the form of a beige foam. TLC: dichloromethane/methanol/conc. ammonia (90:9:0.5) $R_f$=0.38. $^1$H-NMR (200 MHz, $D_2O$): rotameric mixture; δ: 8.28–8.08 (m, 2H), 7.94–7.79 (m, 1H), 7.60–7.40 (m, 2H), 7.21–7.02 (m, 2H), 5.40–5.22 (m, 0.5H), 4.85–4.68 (m, 0.5H), 4.00–3.86 (m, 0.5H), 3.56–3.00 (m, 3H), 2.82–2.70 (m, 0.5H), 2.20–1.86 (m, 2H), 1.6–1.2 (m, 2H).

EXAMPLE 7

Tablets, each comprising 50 mg of (2R,4S)-N-[1-(3,5-bis-trifluoromethyl-benzoyl)-2-benzyl-piperidin-4-yl]-quinoline-4-carboxamide or a salt, for example the hydrochloride, thereof, can be prepared as follows:

| Composition (10 000 tablets) | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of potato starch and the mixture is moistened with an ethanolic solution of the gelatin and granulated through a sieve. After drying, the remainder of the potato starch, the magnesium stearate, the talc and the silicon dioxide are mixed in and the mixture is compressed to form tablets, each weighing 145.0 mg and comprising 50.0 mg of active ingredient; the tablets may, if desired, be provided with breaking notches for finer adaptation of the dose.

EXAMPLE 8

Film-coated tablets, each comprising 100 mg of (2R,4S)-N-[1-(3,5-bis-trifluoromethyl-benzoyl)-2-benzyl-piperidin4-yl]-quinoline4-carboxamide or a salt, for example the hydrochloride, thereof, can be prepared as follows:

| Composition (for 1000 film-coated tablets) | |
|---|---|
| active ingredient | 100.0 g |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed and moistened with a paste prepared from 15 g of corn starch and water (with heating) and granulated. The granules are dried, the remainder of the corn starch, the talcum and the calcium stearate are added and mixed with the granules. The mixture is compressed to form tablets (weight: 280 mg) which are then film-coated with a solution of the hydroxypropylmethylcellulose and the shellac in methylene chloride; final weight of the film-coated tablet: 283 mg.

EXAMPLE 9

Hard gelatin capsules, comprising 100 mg of active ingredient, for example. (2R,4S)-N-[1-(3,5-bis-trifluoromethyl-benzoyl)-2-benzyl-piperidin-4-yl]-quinoline4-carboxamide or a salt, for example the hydrochloride, thereof, can be prepared, for example, as follows:

| Composition (for 1000 capsules) | |
|---|---|
| active ingredient | 100.0 g |
| lactose | 250.0 g |

-continued

| Composition (for 1000 capsules) | |
|---|---|
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve of 0.2 mm mesh size. The two components are intimately mixed. Then first the lactose is added through a sieve of 0.6 mm mesh size and then the microcrystalline cellulose is added through a sieve of 0.9 mm mesh size. The mixture is then intimately mixed again for 10 minutes. Finally the magnesium stearate is added through a sieve of 0.8 mm mesh size. After mixing for a further 3 minutes, size 0 hard gelatin capsules are each filled with 390 mg of the resulting formulation.

EXAMPLE 10

In a manner analogous to that described in Examples 7 to 9 above, it is also possible to prepare pharmaceutical compositions comprising a different compound of formula I or IA or a salt thereof in accordance with one of the above Preparation Examples.

What is claimed is:

1. A compound of formula IA

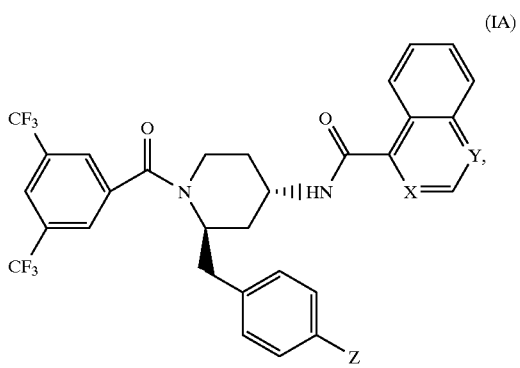

wherein X is CH or N and Y is CH or N, and Z is halogen, or a salt thereof.

2. A compound according to claim 1, wherein Z is chlorine.

3. A compound according to claim 2 selected from the group consisting of (2R,4S)-N-[1-(3,5-bis-trifluoromethyl-benzoyl)-2-(4-chloro-benzyl)-piperidin-4-yl]-quinoline-4-carboxamide; and (2R,4S)-N-[1-(3,5-bis-trifluoromethyl-benzoyl)-2-(4-chloro-benzyl)-piperidinyl]-quinazoline4-carboxamide;

(2R,4S)-N-[1-(3,5-bis-trifluoromethyl-benzoyl)-2-(4-chloro-benzyl)-piperidinyl]-isoquinoline-1-carboxamide;

or in each case a salt thereof.

4. A method for the treatment of disorders induced by substance P comprising administering to a mammal in need thereof a therapeutically effective amount of a compound according to claim 2 or a pharmaceutically acceptable salt thereof.

5. A pharmaceutical composition comprising a compound according to claim 2 or a pharmaceutically acceptable salt thereof.

6. The method of claim 4, wherein the disorder induced by Substance P is a migraine headache.

7. The method of claim 4 wherein the disorder induced by Substance P is an anxiety state.

8. The method of claim 4 wherein the disorder induced by Substance P is vomiting.

9. The method of claim 4 wherein the disorder induced by Substance P is selected from the group consisting of schizophrenia and depression.

10. The method of claim 4 wherein the disorder induced by Substance P is Parkinson's disease.

11. The method of claim 4 wherein the disorder induced by Substance P is selected from the group consisting of rheumatoid arthritis, iritis and conjunctivitis.

12. The method of claim 4 wherein the disorder induced by Substance P is selected from the group consisting of asthma and chronic bronchitis.

13. The method of claim 4 wherein the disorder induced by Substance P is selected from the group consisting of ulcerative colitis and Crohn's disease.

14. The method of claim 4 wherein the disorder induced by Substance P is hypertension.

* * * * *